United States Patent [19]

Kerjean

[11] Patent Number: 5,448,611
[45] Date of Patent: Sep. 5, 1995

[54] PROCESS AND APPARATUS FOR THE TREATMENT OF LESIONS BY HIGH FREQUENCY RADIATION

[75] Inventor: Joël-Theophile Kerjean, Saint Herblain, France

[73] Assignee: Framatome Societe Anonyme, Paris La Defense, France

[21] Appl. No.: 101,354

[22] Filed: Aug. 3, 1993

[30] Foreign Application Priority Data

Aug. 4, 1992 [FR] France ............................. 92 09668

[51] Int. Cl.[6] ............................................. A61N 5/10
[52] U.S. Cl. ......................................... 378/65; 378/147
[58] Field of Search ................................. 378/147, 65

[56] References Cited

U.S. PATENT DOCUMENTS 4,780,898 10/1988 Sundqvist .
4,827,491 5/1989 Barish .................................. 378/147
5,028,789 7/1991 Whittemore .

FOREIGN PATENT DOCUMENTS 0056552 7/1982 European Pat. Off. .
2414242 8/1979 France .
2351450 4/1975 Germany .
WO92/08235 5/1992 WIPO .

*Primary Examiner*—Craig E. Church
*Attorney, Agent, or Firm*—Young & Thompson

[57] ABSTRACT

Method and gamma ray collimator for the treatment of cerebral lesions by gamma irradiation. Gamma rays from a source radiate into an annular substantially divergent path made of radiation absorbing material. At the outlet of this divergent path, ribs further absorb unwanted parasitic oblique radiation. The annular beam of radiation thus formed enters an annular substantially convergent path to exit and to converge in an area to be treated. The annular beam of gamma rays that emerges through both divergent and convergent paths has a sufficient intensity to constitute a lethal dose within a defined volume and obviates the need for long term exposure to point beams of gamma radiation.

10 Claims, 4 Drawing Sheets

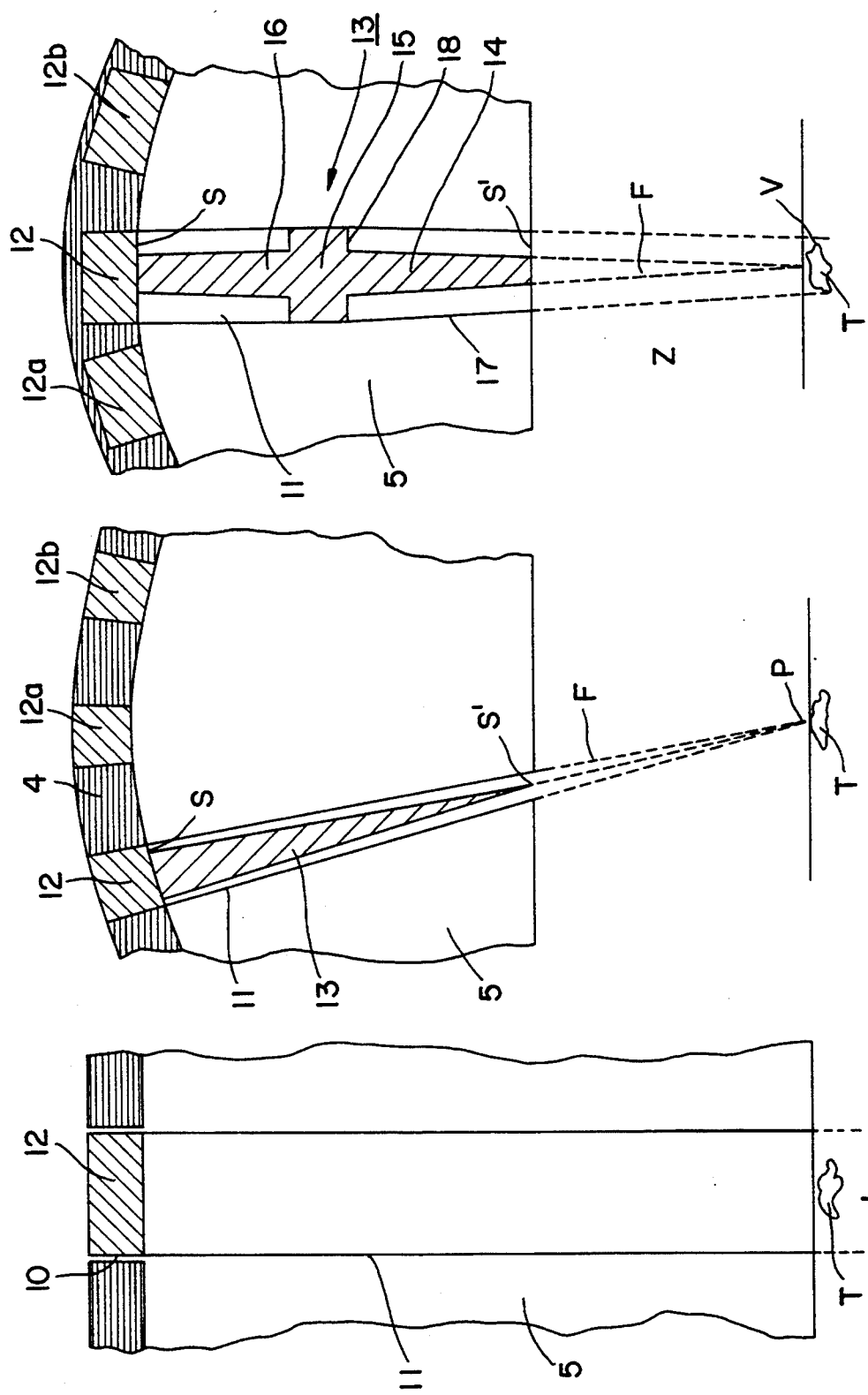

PROCESS AND APPARATUS FOR THE TREATMENT OF LESIONS BY HIGH FREQUENCY RADIATION

BACKGROUND OF THE INVENTION

1. Field of the Invention

The present invention relates to a process for the treatment of lesions by high energy radiation.

It relates more particularly to a process for the irradiation of cerebral lesions by use of a source of gamma rays associated with a collimator.

The invention also relates to a treatment device using the process.

2. Description of the Related Art

In gamma radiation apparatus used at present, the destruction of cerebral lesions treated by non-intrusive neurosurgery is obtained by the precise focusing of gamma radiation on the tumor to be treated. This destruction has to be done very carefully as to the doses of radiation received and absorbed by the healthy tissues.

According to a first known method, there is used a very intense single source whose radiation is focussed by a collimator in a slender cylindrical beam. The intensity of this single beam requires the application of a continuous orbital movement about the lesion to be treated so as to avoid the destruction of intermediate tissue traversed by the very high activity beam.

The continuous orbital movement is obtained by motorization of the heavy components which are the source carrier, the collimator and the associated shields.

According to a second known method, the risk of destruction of healthy tissue is reduced by the use of an assembly of sources whose individual intensity could not cause lesions in the healthy tissues. In return, the individual focussing of each of these sources generates conjointly an integrated dose sufficient for the treatment of the lesion itself.

The above method, as described for example in U.S. Pat. No. 4,780,898, requires the implantation of radioactive sources of very small diameter, generally of the order of a millimeter, and of their respective collimator. These collimators, incorporated in shields generally of lead, are typically about 200 in number and their machining requires long and costly operations. Moreover, the sources are spaced from the focal point and a great portion of their energy is converted to heat by the absorption of the radiation by the components themselves. As a result, only a small part of the radiation passes through the bore serving as a collimator and thus constitutes the only useful radiation for the treatment.

This method has drawbacks which on the one hand are technological connected to the geometry of the components and to the low output of the sources, and on the other hand economic by the absence of optimization of costly components.

There has also been studied an apparatus seeking to eliminate the major defects of the methods described above by limiting the telecontrol of the heaviest components and by decreasing the number of sources and their associated collimating device.

Research carried out has permitted controlling the relative displacement of the sources and of the patient as well as the energy necessary for point treatment of the tumors.

However, this point treatment, although it renders possible the treatment of the surface of a tumor by relative displacement, requires a relatively great duration of irradiation and does not satisfy completely the therapies which seek to obtain a lethal dose in a strictly limited volume corresponding to the dimensions of the tumor to be treated.

SUMMARY OF THE INVENTION

So as to overcome these drawbacks of the known processes and apparatus, the present invention has for its object the process for the control of a gamma radiation beam for the treatment by irradiation and in particular for the treatment of cerebral lesions, characterized in that there is focused, in a first step, the radiation from a source according to a substantially divergent annular path, then in a second step there is cut off the annular beam thus created of the oblique radiation engendered, and in a final step, the annular beam is focused on a substantially convergent annular path to obtain a volumetric focal spot of intensity and size corresponding to the treatment of a lesion of a given volume.

According to a particular characteristic, the use of a bundle of divergent focused radiation followed by convergent focusing permits the optimization of the energy of the source and the obtention of a higher gradient of decrease in the occultation zone of the source.

The invention concerns also an apparatus for the treatment of lesions comprising at least one radioactive source associated with components such as a collimator, shields and adjustment members, characterized in that the collimator comprises a male absorbent element of divergent-convergent profile.

According to the invention, the male portion comprises in its middle a zone provided with ribs ensuring the absorption of peripheral parasitic radiation.

According to an essential characteristic, the profiles of the male portion and of the channel forming the female portion of the collimator are complementary and define an annular diverging-converging space permitting the obtention of a focused spot.

BRIEF DESCRIPTION OF THE DRAWINGS

The invention will be better understood with the aid of the non-limiting example which will be described and the drawings which are attached and in which:

FIG. 2 shows schematically three focusing devices, FIG. 2a representing the prior art constituted by a single source of high intensity, FIG. 2b representing a source-collimator assembly for point irradiation, FIG. 2c representing a source-collimator assembly for volumetric irradiation;

DESCRIPTION OF THE PREFERRED EMBODIMENTS

Figure 1:
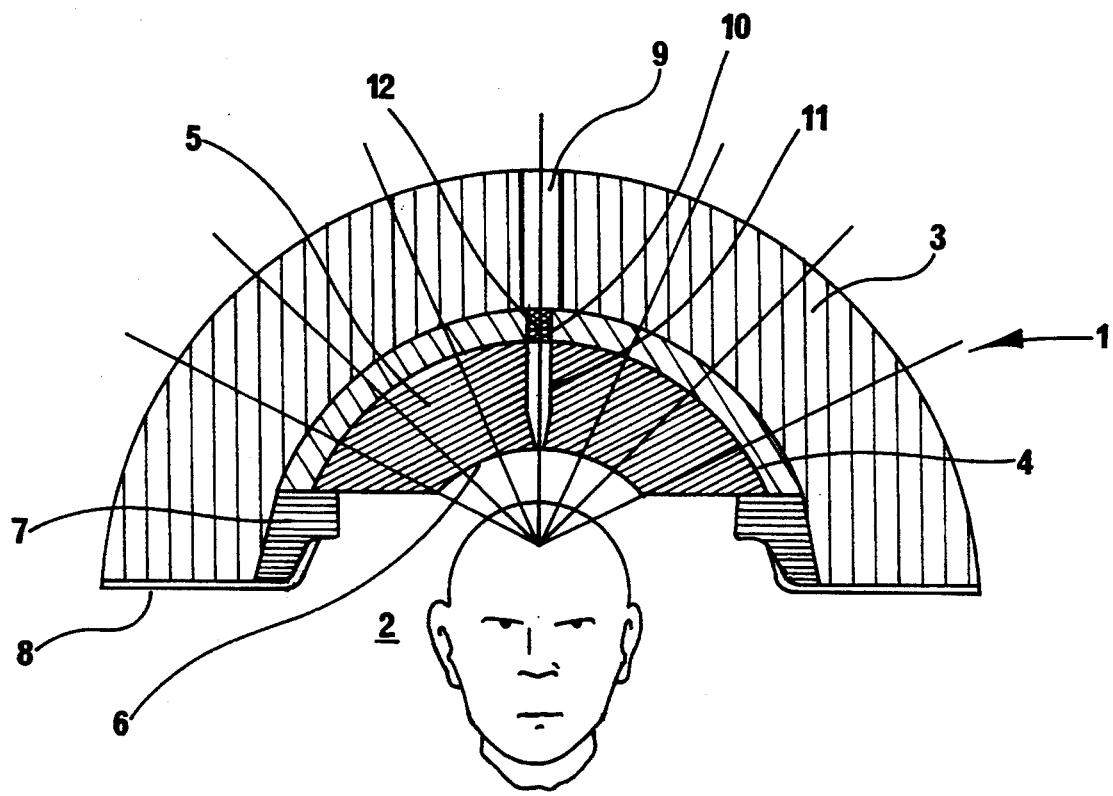
FIG. 1 is a front cross-sectional view of the assembly of source-collimator-shielding of a treatment apparatus to which the invention is applied.

FIG. 1 shows the assembly 1 comprising source carriers and collimator carriers of an apparatus for the treatment of cerebral lesions.

This assembly 1 has the shape of a half-sphere whose open side 2 permits letting pass a table, not shown, supporting the patient.

This assembly comprises an external shield 3 constituted by a substantial thickness of lead, a perforated shelf 4 constituting the carrier of the sources and a collimator carrier 5 of substantial thickness defining an internal spherical surface 6.

The source carrier 4 and the collimator carrier 5 are removably secured to the shielding 3 by means of a ring 7 maintained by an annular flange 8.

This assembly is traversed throughout by radial channels 9, 10 and 11 disposed in such manner that their respective axes converge toward the center of the half-sphere.

These channels, of which a single aligned one is shown in FIG. 1, perform three different functions. Namely, the channel 9 permits the handling, the maintenance and the shielding of a radioactive source 12 particularly a source of Cesium 137. The source 12 is positioned in the channel 10 such that its surface is flush with the end of collimator channel 11.

The collimator channels 11 are machined in the collimator carrier 5 constituted of a material strongly absorbent of gamma rays. These materials are preferably pure lead or an alloy thereof, tungsten, natural uranium, uranium impoverished in isotope 235, covered or not with an inoxidizable alloy. It will be noted that the best results are obtained with the couple Cesium 137, Uranium (natural or impoverished).

As shown in FIG. 2a, the prior art uses gamma ray collimators constituted by a single source, very often of cobalt, associated with a simple bore 11 in which the source generates a ray of useful width L.

This arrangement has drawbacks of which the principal one is constituted by the destruction of healthy tissue surrounding the lesion T and subjected to the same dose of irradiation as the latter.

This arrangement moreover requires the use of high intensity sources of which an important portion of the radiation emitted is absorbed and transformed into heat in the material of the collimator holders 5, which results in low output at an excessive cost.

FIG. 2b shows schematically a source carrier assembly 4 provided with several sources 12, 12a, 12b of gamma rays of a diameter of about 10 millimeters. These sources 12, 12a, 12b are disposed in the channels 10 of the source carrier 4 and are thus positioned in line with the collimator channels 11.

As shown at the left of FIG. 2b, the collimator channel 11 is of conical shape whose base has a diameter near the external diameter of the source 12 and whose summit has a section of a diameter less than this latter, thus defining, between these diameters, a convergent path. The conical wall of this channel 11 focuses the gamma radiation while limiting the parasitic absorption by the mass of the material of the collimator carrier 5. This focusing is however improved by the presence of a male absorbent element 13 of conical shape disposed at the center of channel 11 and in contact with the source 12 at its base.

This geometry defined by two cones of the same summit and whose bases determine a useful emissive surface of annular shape S, provide a spectrum of maximized flux at the summit S' common to the two cones. It will be noted that the internal cone is defined by the surface of the male portion or needle 13 which is preferably of the same absorbent material as the material of the collimator carrier 5 receiving the channels 11 whose wall defines the external cone. This material is essentially uranium either in natural form or in its form impoverished in isotope 235.

The maximized flux F at the outlet of channel 11 defines an annular focused beam such that its generating lines converge at a point P on the target constituted by the lesion T.

It is evident that the respective diameters of the channel 11 and the needle 13 are calculated to obtain a focal point P the most precise possible and at the same time a maximum power of the annular beam at this point.

This embodiment is limited by this compromise because it is inherent that, if one increases the useful section of the annular ray to use the maximum intensity of the source and thus increase the power of radiation on the lesion T, the convergence of the rays takes place in a plane too distant to remain effective.

Finally, FIG. 2c shows an embodiment according to the invention in which the collimation of the gamma radiation from a radioactive source of the type Cesium 137 permits obtaining a given dosage of irradiation in a defined volume V.

Thus, the therapy seeks to reduce the long duration of irradiation necessary during treatments by point beams and seeks to obtain a lethal dose in a defined volume, which is fairly reduced but suitable for the smallest lesions to be treated.

The treatment of these lesions of the order of several millimeters of thickness obviously requires that the decrease of the dose will be as great as possible beyond the treated volume.

FIG. 2c shows in schematic manner a needle 13 constituting the collimator of the invention permitting obtaining a focused volumetric spot V or target volume thereby ensuring complete irradiation of the lesion.

This needle 13 is comprised by a terminal portion 14 contiguous to the summits of the two cones formed respectively by the surface of said portion 14 and the surface 17 of the channel 11, thereby ensuring the creation and the control of an annular beam S' whose generating lines converge toward the lesion T and define the target volume V.

A median portion 15, comprising uranium ribs 18, is disposed such that the ribs 18 deliver in the conical generator interval of the annular beam S' a maximum controlled and "tranquilized" flux, which is to say flux with the peripheral oblique rays cut off.

A truncated conical portion 16, whose base is situated at the median portion 15 and whose summit bears against the surface of a source 12, defines with the surface of the wall of the channel 11 an annular space of divergent shape having a surface S of a size greater than the contact surface with the median ribbed portion 15.

The novel geometry of the needle 13, which ensures the creation and the control of a beam useful over a homogeneous range or a larger volume, thus permits extracting a greater intensity from the source while increasing the gradient of decrease in the zone of occultation Z of the source.

Figure 6:
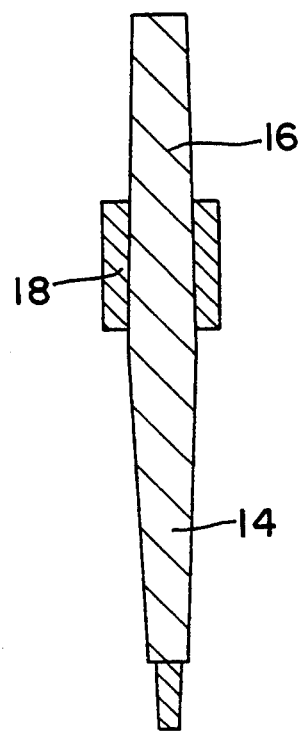
FIG. 6 is a cross-sectional view of the male portion of the collimator of FIG. 3, the male portion being provided with a telescopic structure.

In a preferred embodiment of the invention, not shown, it is possible to provide that at least one of the elements from the following group, terminal portion 14, median portion 15, truncated conical portion 16 of the needle 13 is given a relative movement so as to cause to vary the wide range of the volume V of focusing. Thus, by way of example, the terminal portion 14 of the needle 13 can be constituted by a telescopic cone (FIG. 6)

so as to be able to have the summit of the channel 17 protruding, or retracted from this latter, or flush with this latter, thereby causing the obtained beam to vary.

This geometry has the general shape of two cones assembled at their bases and of opposite summits defining thus an assembly having a divergent-convergent profile.

Figure 3:
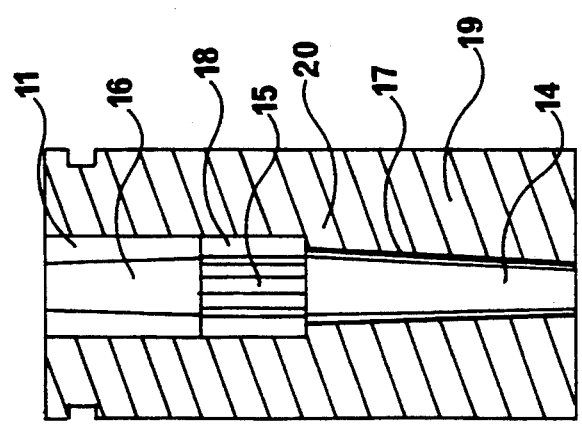
FIG. 3 is a cross-sectional view of a collimator according to the invention.

FIG. 3 shows an embodiment according to FIG. 2c in which the collimator 13 is disposed in a block 19 used as shielding.

The collimator 13 and the block 19 are of natural or impoverished uranium. The collimator 13 and the block 19 may be covered by a protective layer of lead about 1 millimeter thick to improve the output filtration.

FIG. 3 shows in detail the collimator 13 positioned in the channels 11 and 17. As an example, the channel 11 is constituted by a bore of a diameter of 19 mm, adapted to coact with a source of Cesium 137, 20 mm in diameter. The channel 17 is itself of truncated conical form and has a base 15 mm wide and a summit 10 mm wide.

The median portion 15 is positioned in the bore 11 with a slight play and the lower part of the ribs 18 rest on a shoulder 20 provided at the junction of the channels 11 and 17.

Figure 5:
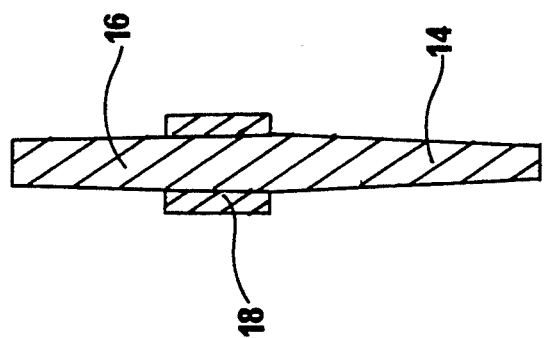
FIG. 5 is a cross-sectional view of the male portion of the collimator of FIG. 3.

The male needle 13 is itself dimensioned to coact with the profile of the channels 11 and 17. As an example, the needle has a median diameter of 10 mm while its ends are reduced to diameters of 7 or 9 mm as shown in FIG. 5.

Figure 4:
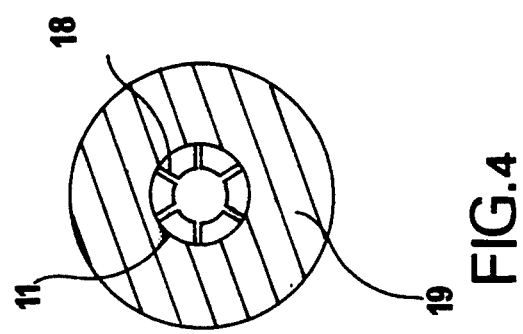
FIG. 4 is a detailed view on a section of the median portion of the collimator of FIG. 3.

FIG. 4 shows in cross section the distribution of the ribs which are six in number, but it is evident that this median portion 15 could be provided with a different number adapted to the desired intensity of the beam.

There will now be described the process of operation of the installation.

After having determined the dimensions of the lesion T, the patient is positioned at the irradiation site 2 served by the assembly of source carrier and collimator carrier 1. A shield of absorbent material, not shown, is then removed and the treatment of the lesion T takes place by an assembly of sources-collimators operating as follows.

The source 12 emits its gamma radiation along an azimuthal diffusion. This radiation is, in this first stage, focused by the walls of the channel 11 to produce a usable beam of radiation. This focusing is completed by the focusing obtained thanks to the wall of the truncated conical portion 16 which slightly shadows the surface of the source 12, which permits obtaining an annular beam S which amplifies along the annular path defined by the substantially divergent walls.

This amplification has as a result the risk of creating oblique parasitic radiation which reduces the efficiency of the source and renders difficultly controllable the action of the beam on the healthy tissues in the zone Z of shaded from irradiation from the source.

The amplified annular beam then penetrates into the intermediate portion 13 provided with ribs 18. In this second stage, the ribs cut off the oblique rays near the generating lines of the hyperboloid constituted by the annular beam.

This cut-off beam F whose emissions are controlled is in the form of an annular stream of the fluid type at the entry of a third stage for control of its focusing.

The beam, midway along the collimator, thus has maximum power.

In the third stage, the terminal portion controls the beam and focuses it causing it to follow, thanks to the walls, an annular oblique path such that the assembly of the generating lines constituting this annular beam F converge to a zone corresponding to the position of the lesion T where they define a target volume V of size and intensity necessary for the treatment of a lesion T of a given volume.

The invention is not limited to the embodiments described above. It involves on the contrary all the variations and in particular it protects all methods of control of an annular beam from the time the treatment of the cerebral lesion is effectuated with the aid of an annular beam used for point irradiation or volumetric irradiation.

I claim:

1. Process for the collimation of a beam of gamma rays for the treatment of cerebral lesions, comprising the following steps:
   directing the radiation from a source of gamma radiation along an annular, substantially divergent path made of a radiation absorbing material to form an annular beam of gamma rays;
   removing from said annular beam, by absorption into said radiation absorbing material, those gamma rays which do not travel along said substantially divergent path; and
   directing said annular beam along an annular, substantially convergent path to obtain, at an outlet of said convergent path, a volumetric area of gamma radiation of a given intensity, said area being of a sufficient size for the treatment of a cerebral lesion of a given volume.

2. Process according to claim 1, wherein said annular divergent path and said convergent path define an annular beam of controlled emission.

3. Process according to claim 2, wherein ribs made of said absorbent material are provided between said divergent and convergent paths and absorb parasitic radiation, thus contributing to a sharp decrease in irradiation beyond said area to be treated.

4. Apparatus for the treatment of cerebral lesions by a beam of gamma radiation comprising at least one radioactive source in an assembly comprising at least one source carrier and a collimator carrier, a collimator channel, and a male absorbent element contained in said collimator channel, said collimator channel and said male absorbent element defining an annular space of convergent shape.

5. Apparatus according to claim 4, wherein said male absorbent element has a divergent-convergent profile constituted by two portions of conical shape assembled at their bases.

6. Apparatus according to claim 5, wherein said male absorbent element comprises a median portion provided with ribs for absorbing peripheral oblique rays which do not follow said annular space.

7. Apparatus according to claim 5, wherein at least one of the two portions of the male absorbent element has a telescopic structure whereby a summit of said male absorbent article retracts or protrudes from an outlet of said collimator channel to vary a convergence point of said beam and a target volume of irradiation.

8. Apparatus according to claim 4, further comprising external shields source on said carrier, and wherein said external shields, source carrier, collimator carrier, and male element are of a same absorbent material which absorbs radiation.

9. Apparatus according to claim 8, wherein said absorbent material is one of natural uranium and impoverished uranium in isotope 235.

10. Apparatus according to claim 4, wherein said collimator channel comprises a lead protective sheath to filter the radiations at the outlet of the collimator.

* * * * *